United States Patent
Waldmann

(10) Patent No.: US 7,137,946 B2
(45) Date of Patent: Nov. 21, 2006

(54) ELECTROPHYSIOLOGICAL MEASUREMENT METHOD AND SYSTEM FOR POSITIONING AN IMPLANTABLE, HEARING INSTRUMENT TRANSDUCER

(75) Inventor: Bernd Waldmann, Boulder, CO (US)

(73) Assignee: Otologics LLC, Boulder, CO (US)

( * ) Notice: Subject to any disclaimer, the term of this patent is extended or adjusted under 35 U.S.C. 154(b) by 66 days.

(21) Appl. No.: 11/010,208

(22) Filed: Dec. 11, 2004

(65) Prior Publication Data

US 2005/0131272 A1     Jun. 16, 2005

Related U.S. Application Data

(60) Provisional application No. 60/528,728, filed on Dec. 11, 2003.

(51) Int. Cl.
    H04R 25/00    (2006.01)
(52) U.S. Cl. .................. 600/25; 600/559; 381/60
(58) Field of Classification Search .............. 600/25, 600/379, 559; 607/55–57; 623/10; 381/56–60, 381/312–331; 181/126–137
    See application file for complete search history.

(56) References Cited

U.S. PATENT DOCUMENTS

| | | | |
|---|---|---|---|
| 3,752,939 A | 8/1973 | Bartz | 607/57 |
| 3,902,084 A | 8/1975 | May, Jr. | 310/8.1 |
| 3,902,085 A | 8/1975 | Bizzigotti | 310/8.3 |
| 4,428,377 A | 1/1984 | Zollner et al. | 128/419 |
| 4,441,210 A | 4/1984 | Hochmair et al. | 455/41 |
| 4,944,301 A | 7/1990 | Widin et al. | 128/420.6 |
| 4,947,844 A | 8/1990 | McDermott | 128/421 |
| 4,988,333 A | 1/1991 | Engebretson et al. | 600/25 |
| 5,024,224 A | 6/1991 | Engebretson | 128/420.6 |
| 5,061,282 A | 10/1991 | Jacobs | 623/10 |
| 5,069,210 A | 12/1991 | Jeutter et al. | 128/420.6 |
| 5,085,628 A | 2/1992 | Engebretson et al. | 600/25 |
| 5,217,011 A | 6/1993 | Bisch | 128/420.6 |
| 5,282,858 A | 2/1994 | Bisch et al. | 623/10 |
| 5,531,774 A | 7/1996 | Schulman et al. | 607/56 |
| 5,553,152 A | 9/1996 | Newton | 381/68.6 |
| 5,554,096 A | 9/1996 | Ball | 600/25 |
| 5,569,307 A | 10/1996 | Schulman et al. | 607/56 |
| 5,571,148 A | 11/1996 | Loeb et al. | 607/57 |
| 5,603,726 A | 2/1997 | Schulman et al. | 607/57 |
| 5,609,616 A | 3/1997 | Schulman et al. | 607/56 |
| 5,624,376 A | 4/1997 | Ball et al. | 600/25 |
| 5,702,342 A | 12/1997 | Metzler et al. | 600/25 |
| 5,707,338 A | 1/1998 | Adams et al. | 600/25 |
| 5,772,575 A | 6/1998 | Lesinski et al. | 600/25 |

(Continued)

OTHER PUBLICATIONS

Biopac Systems, Inc., Auditory Brainstem Response (ABR) Testing, [Retrieved on Nov. 24, 2003]. Retrieved from the Internet <URL: www.biopac.com/AppNotes/app105ABR/ABRTesting.htm.

(Continued)

*Primary Examiner*—John P. Lacyk
(74) *Attorney, Agent, or Firm*—Marsh Fischmann & Breyfogle LLP

(57) ABSTRACT

An electrophysiological measurement method and system is provided for positioning an implantable transducer of a hearing instrument relative to a middle ear component or inner ear of a patient. The method and system employ electrophysiological measurement signals obtained in response to test signals applied to an implanted transducer. In one embodiment, the electrophysiological measurements are obtained by an electrocochleography measurement device that measures the cochlear summating potential and/or action potential responsive to test signals applied to an implanted transducer. In another embodiment, an auditory brainstem response measurement device is utilized to obtain electrical potential measurement signals responsive to test signals applied to an implanted transducer.

26 Claims, 7 Drawing Sheets

U.S. PATENT DOCUMENTS

| | | | |
|---|---|---|---|
| 5,776,172 A | 7/1998 | Schulman et al. | 607/56 |
| 5,788,711 A | 8/1998 | Lehner et al. | 600/25 |
| 5,842,967 A | 12/1998 | Kroll | 600/25 |
| 5,857,958 A | 1/1999 | Ball et al. | 600/25 |
| 5,876,425 A | 3/1999 | Gord et al. | 607/56 |
| 5,879,283 A | 3/1999 | Adams et al. | 600/25 |
| 5,899,847 A | 5/1999 | Adams et al. | 600/25 |
| 5,938,691 A | 8/1999 | Schulman et al. | 607/57 |
| 5,954,628 A | 9/1999 | Kennedy | 600/25 |
| 5,991,663 A | 11/1999 | Irlicht et al. | 607/57 |
| 5,993,376 A | 11/1999 | Kennedy | 600/25 |
| 5,999,856 A | 12/1999 | Kennedy | 607/57 |
| 6,001,129 A | 12/1999 | Bushek et al. | 623/10 |
| 6,005,955 A | 12/1999 | Kroll et al. | 381/328 |
| 6,077,215 A | 6/2000 | Leysieffer | 600/25 |
| 6,154,023 A | 11/2000 | Durand | 324/117 R |
| 6,293,903 B1 | 9/2001 | Kasic, II et al. | 600/25 |
| 6,342,035 B1 | 1/2002 | Kroll et al. | 600/25 |
| 6,390,970 B1 | 5/2002 | Muller | 600/25 |
| 6,398,717 B1 | 6/2002 | Leysieffer et al. | 600/25 |
| 6,491,622 B1 | 12/2002 | Kasic, II et al. | 600/25 |
| 6,517,476 B1 | 2/2003 | Bedoya et al. | 600/25 |
| 6,537,201 B1 | 3/2003 | Kasic, II et al. | 600/25 |
| 6,540,661 B1 | 4/2003 | Muller | 600/25 |
| 6,554,762 B1 | 4/2003 | Leysieffer | 600/25 |
| 6,620,094 B1 | 9/2003 | Miller | 600/25 |
| 6,705,985 B1 | 3/2004 | Easter et al. | 600/25 |
| 6,707,920 B1 | 3/2004 | Miller | 381/326 |
| 6,712,754 B1 | 3/2004 | Miller et al. | 600/25 |
| 6,726,618 B1 | 4/2004 | Miller | 600/25 |
| 2002/0026091 A1 | 2/2002 | Leysieffer | 600/25 |

OTHER PUBLICATIONS

Scott, M., and Bhattacharyya, N., Auditory Brainstem Response Audiometry, [Retrieved on Nov. 24, 2003]. Retrieved from eMedicine.com website using the Internet<URL: http://emedicine.com/ent/topic47.

Hain, T.C., Vestibular Testing, [Retrieved on Nov. 24, 2003]. Retrieved from the Internet <URL: http://www.tchain.com/otoneurology/testing/engrot.html.

NIDCD, Meniere's Disease, [Retrieved on Nov. 24, 2003]. Retrieved from the National Institute on Deafness and Other Communications Disorders website using the Internet <URL: http://nidcd.nih.gov/health/balance/meniere.asp.

Levenson, M.J., Meniere's Disease, [Retrieved on Nov. 24, 2003]. Retrieved from the Ear Surgery Information Center website using the Internet <URL: http://www.earsurgery.org/meniere.html.

Hain, T.C., Hearing Testing, [Retrieved on Nov. 24, 2003]. Retrieved from the Internet <URL: http://www.tchain.com/otoneurology/testing/hearing_testing.htm.

Baylor College of Medicine, Core Curriculum Syllabus, Audiology, [Retrieved on Nov. 24, 2003]. Retrieved from the Baylor College of Medicine website using the Internet <URL: http://www.bcm.tmc/oto/studs/aud.html.

Meniere's Disease Information Center, Electrocochleography and Meniere's Disease, [Retrieved on Nov. 24, 2003]. Retrieved from the Meniere's Disease Information Center website using the Internet <URL: http://www.menieresinfo.com/ecog.html.

Frederickson, et al., *Ongoing Investigations into an Implantable Electromagnetic Hearing Aid for Moderate to Severe Sensorineural Hearing Loss*, pp. 107-120, Feb. 1995, *Otolaryngologic Clinics of North America*, vol. 28, No. 1.

Frederickson, et al., *Current Status in the Development of Implantable Middle Ear Hearing Aids*, pp. 189-204, 1996, *Advances in Otolaryngology*, vol. 10, Mosby Year Book.

Wilson, et al., Implantable Hearing Aids: Changes in the Auditory-Evoked Potential of the Monkey in Response to Increased Loading of the Stapes, pp. 149-252, 1990, *American Journal of Otolaryngoly*.

Park, et al., Use of Distortion Product Otoacoustic Emissions to Assess Middle Ear Transducers in Rhesus Monkeys, pp. 576-590, Sep. 1995, *The American Journal of Otology*, vol. 16, No. 5.

Miller and Frederickson, *Audiology Treatment*, pp. 489-510 (Valente, et al., eds., Thieme Medical Publishers 2000).

ELECTROPHYSIOLOGICAL MEASUREMENT METHOD AND SYSTEM FOR POSITIONING AN IMPLANTABLE, HEARING INSTRUMENT TRANSDUCER

CROSS-REFERENCE TO RELATED APPLICATIONS

This application claims priority under 35 U.S.C. §119 to prior U.S. Provisional Patent Application Ser. No. 60/528,728, filed on Dec. 11, 2003, and entitled "ELECTROPHYSIOLOGICAL MEASUREMENT METHOD AND SYSTEM FOR ASSESSING A MIDDLE EAR INTERFACE OF AN IMPLANTABLE HEARING INSTRUMENT TRANSDUCER", the disclosure of which is incorporated herein by reference in its entirety.

FIELD OF THE INVENTION

The present invention relates to the field of hearing instruments that include implanted transducers, and more particularly, to an electrophysiological measurement method and system for positioning an implantable hearing instrument transducer relative to a middle ear component or the inner ear of a patient.

BACKGROUND OF THE INVENTION

In the class of hearing aids generally referred to as implantable hearing instruments, some or all of various hearing augmentation componentry is positioned subcutaneously on or within a patient's skull, typically at locations proximate the mastoid process. In this regard, implantable hearing instruments may be generally divided into two sub-classes, namely semi-implantable and fully implantable. In a semi-implantable hearing instrument, components such as a microphone, signal processor, and transmitter may be externally located to receive, process, and inductively transmit an audio signal to implanted components, e.g. an implantable receiver and transducer. In a fully implantable hearing instrument, all of the components, e.g. the microphone, signal processor, and transducer, may be located subcutaneously. In either arrangement, the implantable transducer is utilized to stimulate a component of the patient's auditory system, e.g. a middle ear component or inner ear.

By way of example, one type of implantable transducer includes an electromechanical transducer having a magnetic coil that drives a vibratory actuator. The actuator is positioned to interface with and stimulate the ossicular chain of the patient via physical engagement. (See, e.g. U.S. Pat. No. 5,702,342). In another approach, implanted excitation coils may be employed to electromagnetically stimulate magnets affixed within the middle ear. (See, e.g. U.S. Pat. No. 5,624,376). In each of these approaches, a changing magnetic field is employed to induce vibration of a middle ear component, e.g. one or more bones of the ossicular chain, thereby stimulating the cochlea through its natural input, i.e. the oval window. In other approaches, an implantable transducer is located within the inner ear or in direct contact with the round window of the inner ear of a patient, wherein vibrations are imparted to the cochlear fluid of the patient. For example, the implantable transducer may be defined by a microactuator that functions like a parallel plate capacitor, wherein applied voltage changes across the "plates" yields electrostatic forces that cause one of the plates to functionally flex as a diaphragm to input vibrations to the cochlear fluid of a patient. (See, e.g. U.S. Pat. No. 5,984,859). In another arrangement, a number of output-side electromechanical transducers may be disposed on or within a mechanical carrier that is positioned within the inner ear. (See e.g. U.S. Pat. No. 6,575,894).

In the case of implantable transducers designed to interface with the ossicular chain, the establishment/maintenance of a desired interface between the implantable transducer and the ossicular chain is important for proper instrument operation. For instance, stimulation of the ossicular chain through vibration relies at least in part on an intimate contact interface between the ossicular chain and transducer. Overloading or biasing of the implantable transducer relative to the ossicular chain can result in degraded performance of the biological aspect (movement of the ossicular chain), possibly causing an additional impairment of hearing, as well as degraded performance of the mechanical aspect (movement of the transducer). Further, if the implantable transducer is underloaded relative to the ossicular chain, e.g. a loose connection or no physical contact at all, vibrations may not be effectively communicated.

Similarly, in the case of implantable transducers designed to interface directly with an inner ear, the establishment/maintenance of a desired interface between the implantable transducer and inner ear is important for proper instrument operation. For example, proper contact positioning of an implantable transducer within or on the outside of the round window of the inner ear is needed for proper stimulation of the cochlear fluid.

As may be appreciated, at the time of implant proper setup of an implantable transducer may depend on the present condition of the middle ear and/or inner ear of a patient. For instance, the positioning of the transducer and the nature of the sound processing parameters may be determined based on patient-specific biological aspects such as damage or reduced mobility of the ossicular chain, etc. Over time, such aspects may change and additional pathological aspects may develop. These changes or developments, in turn, may affect the performance of the implanted transducer, e.g. such as by changing the engagement between the transducer and the ossicular chain or inner ear.

SUMMARY OF THE INVENTION

In view of the foregoing, a primary objective of the present invention is to provide a method and system for positioning an implantable transducer of a semi- or fully-implantable hearing instrument relative to a middle ear component of a patient (e.g. a member of the ossicular chain) or inner ear of a patient.

A further objective of the present invention is to provide a method and system for positioning an implantable hearing instrument transducer relative to a middle ear component or inner ear of a patient in a simplified manner.

Yet a further objective of the present invention is to provide for the positioning an implantable hearing instrument transducer relative to a middle ear component or inner ear of a patient utilizing a method and a system that be may readily employed at the time of implant and/or subsequent to implant to account for pathological changes.

The above-noted objectives and additional advantages are realized in an inventive method and system which provide for the supply of test signals to an implantable hearing instrument transducer, measurement of electrophysiological responses thereto so as to yield corresponding measurement signals, and processing of the measurement signals to provide an output signal indicative of the desirability of the position of the implantable transducer. By utilizing the output signals, the method and system facilitate positioning of the implantable transducer to a desired interface relative to a middle ear component or inner ear of a patient. As may be appreciated, the supply, measurement and processing capabilities may be successively employed as an implantable transducer is successively positioned at a plurality of positions (e.g. advanced and/or retracted relative to a middle ear component or inner ear) until a desired interface is achieved between the implantable transducer and a middle ear component or inner ear. By way of primary example, a desired interface may be realized upon initial implantation of the implantable transducer and/or subsequent thereto after a period of use (e.g. to account for pathological changes over time).

In one embodiment, the electrophysiological measurement may comprise the utilization of an electrocochleography (EC) measurement device to measure the cochlear microphonic, summating potential and/or compound action potential of the auditory nerve in response to test signals applied to the implantable transducer. Such electrocochleography measurement device may include an electrode positionable at the eardrum or within the middle ear of a patient. The positioning of such an electrode may, in some cases, be facilitated by the access to the middle ear afforded by the surgical approach (e.g. atticotomy) used to implant the implantable hearing instrument. In another embodiment, an auditory brainstem response (ABR) measurement device may be employed to measure the electrical potential near the region of the brain (e.g. the dorsal and ventral cochlear nuclei of the brainstem) that processes the cochlear input response to test signals applied to an implantable transducer. In this embodiment, one or more electrodes positionable at various locations on the scalp of a patient may be employed to measure the ABR potentials. In each of the embodiments described above, the devices used to generate the test signals and/or to measure and/or process the detected responses may be disposed external to the patient, or they may be incorporated into the implantable components of the implantable hearing instrument.

Preferably, a source used to provide the test signals may be operatively interconnected with the electrocochleography measurement device so that the measurement signals may be obtained in timed relation to the supply of the test signals. That is, predeterminable time ranges, or time windows, may be established for obtaining the measurements signals after the supply of corresponding test signals. Further, a source may preferably be employed that provides test signals having a plurality of signal portions with different frequencies spread across a predetermined range, e.g. a predetermined range that includes a predetermined or determinable resonant frequency of the implantable transducer being positioned.

As may be appreciated, in either of the noted embodiments processing of the measurement signals may be carried out by a signal processor preprogrammed or otherwise adapted to process the measurement signals according to a predetermined algorithm(s), or control logic, and thereby provide an output signal reflecting the desirability of the position of an implantable transducer relative to a middle ear component or inner ear of a patient. In this regard, for example, processing of the measurement signals may entail the averaging of corresponding, extracted measurement values over successive time periods. Further, measurement signal values, or averaged values thereof, may be compared during processing to predetermined values or to prior measurement signal values or averages thereof to assess whether a desired interface is present between an implantable transducer and a middle ear component or inner ear of a patient. For example, as an implantable transducer is advanced during implantation, successive averaged potential measurement values may be compared until a maximum value is reached, (e.g. corresponding with a maximum amplitude electrophysiological response), thereby indicating a desired interface. Again, the repeated steps of test signal supply, response measurement, and processing/comparison of the measurements values may be carried out according to a control algorithm, as might be implemented in a computer program.

In conjunction with the inventive method and system, the responsive action of positional adjustment of an implantable transducer may be accomplished either manually or by a controllable actuator (e.g. a small motor) so as to make the process of interface optimization partially or completely automated. For example, the processor output signal may be employed as a feedback signal in an automated positioning system, such as that disclosed in U.S. Pat. No. 6,712,754, hereby incorporated by reference.

In a further aspect of the present invention, a user interface may be provided for receiving the processor output signal and providing a user interface output in response thereto, wherein the user interface output provides an indication of the desirability of the positional interface between an implantable transducer and a middle ear component or inner ear of a patient. In this regard, the user interface may comprise either or both of an audio output device and visual output device for providing an indication(s) of the desirability of the positional interface of a implantable transducer relative to a middle ear component or inner ear of a patient. For example, by comparing successive measurement signal values as described above, a maximum value may be identified so that a single audio and/or visual indication may be provided to a user to indicate that an optimal position has been achieved. Alternatively, successive measurement signal values may be processed and provided to the user interface to provide for successive output indications of the desirability of each given position of an implantable transducer as the implantable transducer is being advanced and/or retracted relative to a middle ear component or inner ear.

It should be noted that the present invention is not limited to facilitating and/or automating the adjustment of transducers which impart a purely linear motion along a given axis, and which are adjusted along that axis. For example, an implantable transducer might be constructed to impart a rotary motion to an ossicle (e.g. the incus), wherein the implantable transducer may be brought into a greater or lesser degree of contact with the ossicle as it is rotated. In such a case, the present invention may be employed to facilitate and/or otherwise utilize the measurement signals in the control of the rotary adjustment of the transducer so as to achieve an optimum condition of loading.

Additional aspects and advantages of the present invention will become apparent to those skilled in the art upon consideration of the further description provided hereinbelow.

DETAILED DESCRIPTION

Figure 1:
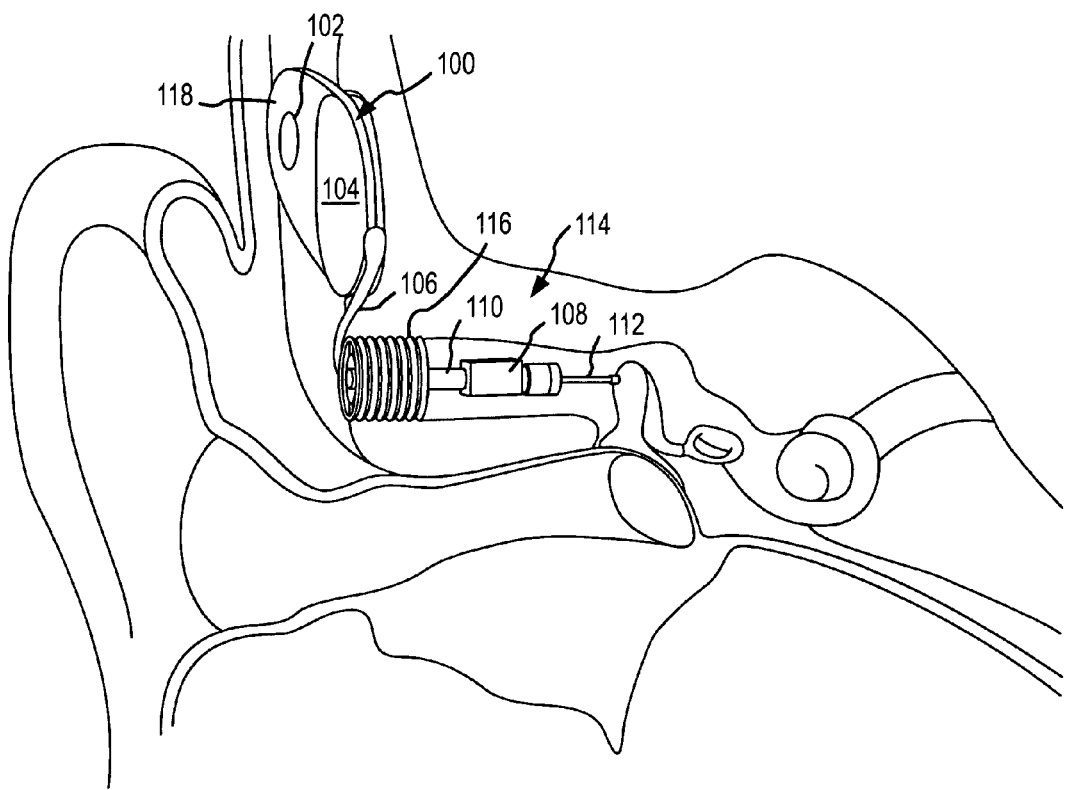
FIGS. 1 and 2 illustrate implantable and external componentry respectively, of a semi-implantable hearing instrument.
Figure 2:
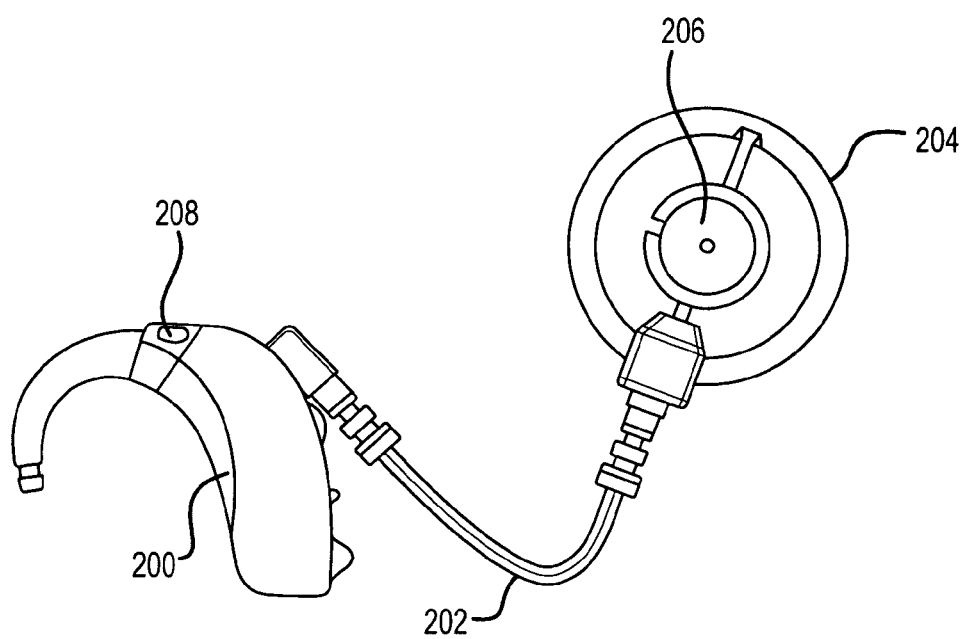

FIGS. 1 and 2 illustrate an example of a semi-implantable hearing instrument for a middle ear implementation. The implanted components are shown in FIG. 1 and the external components are shown in FIG. 2. As will be appreciated, the present invention may also be employed with fully implantable, middle ear hearing instruments, wherein all components of the hearing instrument are located subcutaneously. Further, the present invention may be employed for semi-implantable and/or fully implantable inner ear hearing instruments in which an implantable transducer is positioned relative to the inner ear of a patient, e.g. within the inner ear or in contact relation to the outside of the round window of the inner ear.

In the illustrated system, an implanted biocompatible housing 100 is located subcutaneously on a patient's skull. The housing 100 includes a wireless audio signal link receiver/transmitter 118 (e.g. an RF signal transceiver comprising a coil element) and a signal processor 104 (e.g. comprising processing circuitry and/or a microprocessor). The signal processor 104 is electrically interconnected via wire 106 to an implanted transducer 108 for stimulating a middle ear component of a patient.

The transducer 108 is supportably positioned by a mounting apparatus 116. The mounting apparatus 116 extends through (e.g. via a hole drilled therein) and is attached to a patient's skull, typically within the mastoid process. In the illustrated embodiment, the transducer 108 may be any type of transducer having the ability to transduce electrical inputs into mechanical outputs and vice versa. More broadly, the transducer 108 may include without limitation electromagnetic transducers, piezoelectric transducers, etc.

For purposes of illustration, the transducer 108 will be described as an electromagnetic transducer in the following description. In that regard, the transducer 108 includes an actuator 112, which according to this example, is designed to transmit axial vibrations to a member of a ossicular chain of the patient (e.g. the incus 120). The transducer 108 also includes a driver (not shown on FIG. 1) to drive the actuator 112 in response to transducer drive signals. According to the present transducer example, the driver may include a coil and one or more magnets configured to cause axial, vibratory movement of the actuator 112 and stimulate the ossicular chain to produce or enhance the sensation of sound for the patient.

Referring to FIG. 2, the semi-implantable hearing aid system further includes an external housing 200 comprising a microphone 208 and internally mounted audio signal processing (SSP) unit (not shown). The SSP unit is electrically interconnected via wire 202 to a wireless audio signal link transmitter/receiver 204 (e.g. an RF signal transceiver. comprising a coil element). The external housing 200 is configured for disposition around the rearward aspect of the patient's ear. The external transmitter/receiver 204 and implanted receiver/transmitter 118 may each include magnets 206 and 102, respectively, to facilitate retentive juxtaposed positioning.

During operation, acoustic signals are received at the microphone 208 and processed by the SSP unit within external housing 200. As will be appreciated, the SSP unit may utilize digital processing to provide frequency shaping, amplification, compression, and other signal conditioning, including conditioning based on patient-specific fitting parameters. In turn, the SSP unit via wire 202 provides audio drive signals to the transmitter 204. Where an RF signal link is employed, such drive signals may comprise RF carrier and processed audio drive signal portions. The audio drive signals are transcutaneously transmitted by the external transmitter/receiver 204 to the implanted receiver/transmitter 118. (e.g. via inductive coupling in RF signal link embodiments).

Upon receipt of the audio drive signals, the implanted signal processor 104 processes the signals (e.g. via envelope detection circuitry) to provide a processed drive signal via wire 106 to the transducer 108. According to this example, the drive signals cause the actuator 112 to vibrate at acoustic frequencies to effect the desired sound sensation via mechanical stimulation of the ossicular chain of the patient. As above, an important factor related to proper operation of the described hearing instrument is the interface between the transducer 108, and particularly actuator 112, and the ossicular chain. That is, if a desirable interface has been established, the actuator 112 will readily communicate axial vibrations to the ossicular chain of the patient. On the other hand, if the actuator 112 is "underloaded" (no interconnection or a less than desired connection has been established), axial vibrations may not be communicated or effectively communicated. Further, if the actuator 112 is "overloaded" against the ossicular chain, transmission may be adversely effected. For instance, the patient may experience suboptimal stimulation via the transducer 108, including decreased sensitivity to the action of the transducer 108 or the perception of distortion or noise.

Figure 3:
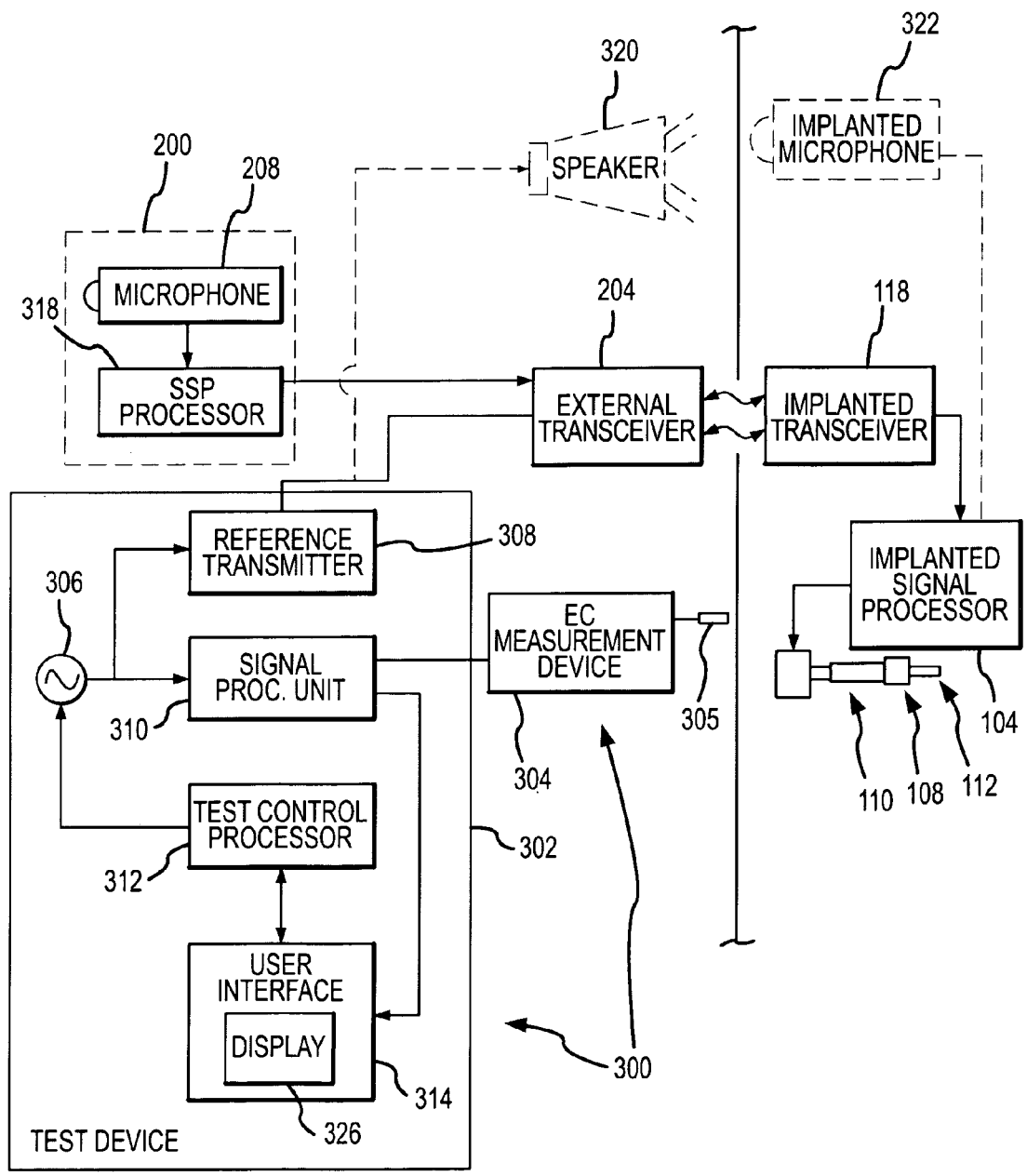
FIG. 3 illustrates one embodiment of the present invention that utilizes an electrocochleography measurement device to assess an interface between an implanted transducer and a middle ear component of a patient.

Referring now to FIG. 3, to facilitate the positioning of an implantable transducer in relation to a middle ear component (e.g. the ossicular chain,) or inner ear, such as the middle ear transducer 108 shown in FIGS. 1 and 2, one embodiment of the present invention includes a measurement system 300 having a test device 302 and an electrocochleography (EC) measurement device 304 interconnected thereto. The electrocochleography measurement device 304 measures the electrical potential(s) associated with the cochlea and/or auditory nerve in response to test signals that are generated by the test device 302 and supplied to the implanted transducer 108. The measured electrical potential(s) may be output as measurement signals by the electrocochleography measurement device 304 to the test device 302 and processed/output to a user to assess whether a desired positional interface between the implantable transducer and a middle ear component of a patient (e.g. a member of the ossicular chain) or inner ear of a patient is present. For example, in middle ear applications, such output may be utilized by medical personnel during implantation procedures to advance or retract a transducer 108 relative to a middle ear component.

More particularly, the electrocochleography measurement device 304 may be provided to measure the cochlear microphonic, summating potential and/or compound action potential of the auditory nerve in response to the noted test signals.

The cochlear microphonic, summating potential is the electrical potential generated at the hair cell level in the cochlea. Typically, such summating potential may have a predeterminable latency range following stimulation. Further, the summating potential may have a predeterminable durational range (e.g. directly related to the test signal duration) and predeterminable absolute amplitude range. Such predeterminable ranges may be employed by test device 302 to facilitate processing of the measured potential values output by electrocochleography measurement device 304.

The action potential of the auditory nerve is an alternating current response that is generated by the cochlear end of the VIII cranial nerve and is typically viewed as representing the summed response of the synchronous firing of thousands of auditory nerve fibers. That is, the size of the action potential reflects the number of nerve fibers which are firing simultaneously. In the absence of adverse pathology, the action potential may have a predeterminable latency range (e.g. about 1.30 milliseconds to 1.70 milliseconds). Its duration may also have a predeterminable range (e.g. about 0.80 milliseconds to 1.25 milliseconds), with a predeterminable absolute amplitude range (e.g. between about 0.60 millivolts and 3.00 millivolts). Such predeterminable ranges may be employed by test device 302 to facilitate processing of the measured potential output from electrocochleography measurement device 304. As may be appreciated, measurement signal values corresponding with the measured magnitude of the summating potential and/or action potential and/or a ratio thereof may be extracted and processed by the test device 302 to assess the interface between the implantable transducer and middle ear component or inner ear of a patient, e.g. transducer 108 in middle ear procedures.

Figure 4:
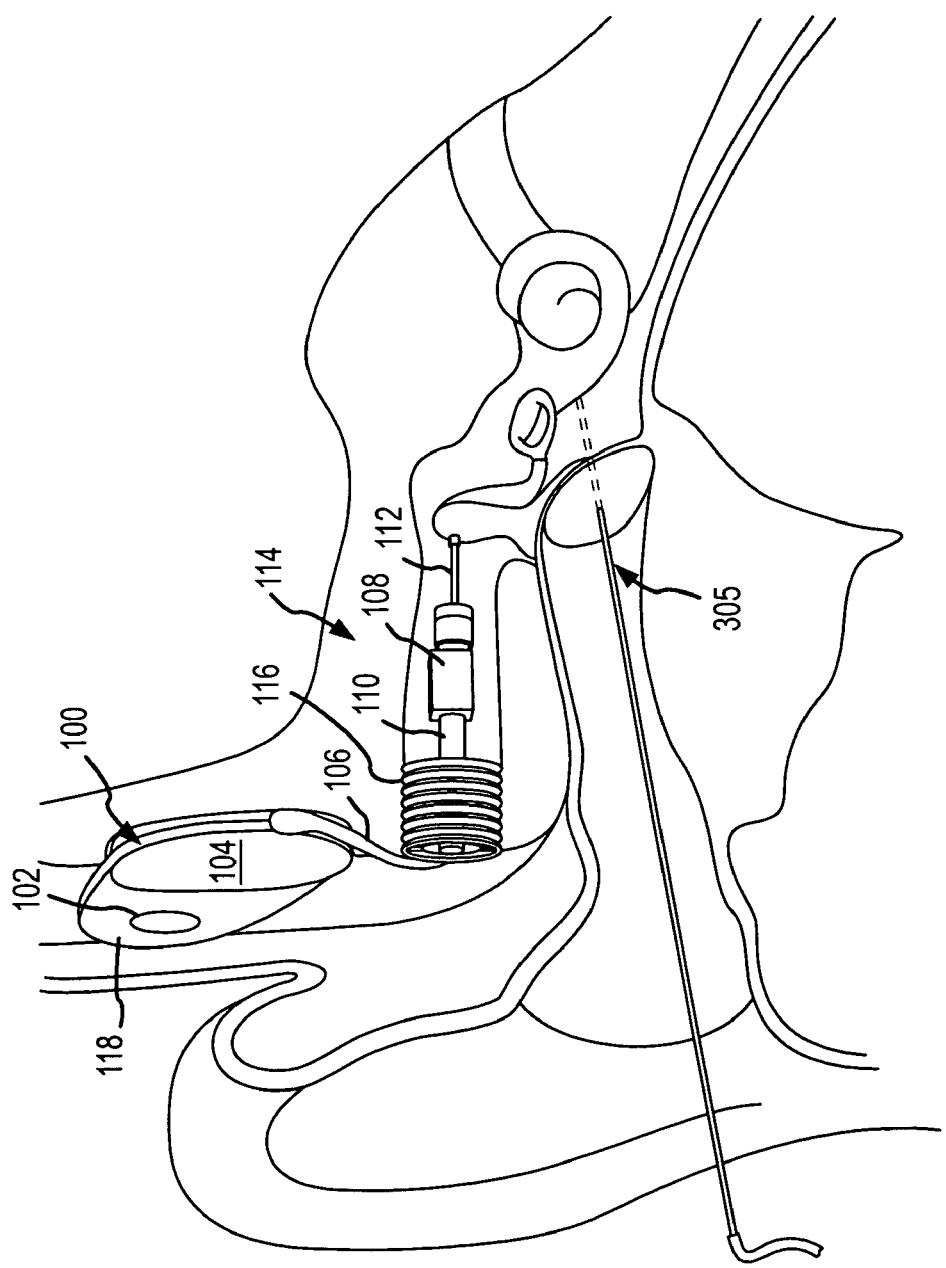
FIG. 4 illustrates an electrocochleography measurement electrode of the embodiment of FIG. 3.

To measure the summating potential and/or action potential, the electrocochleography measurement device 304 may comprise one or more electrodes 305. As shown in FIG. 4, an electrocochleography measurement electrode 305 may be positioned so that a distal end thereof is located immediately adjacent to the eardrum of a patient. Optionally, a small opening may be defined in the eardrum for advancement of the electrocochleography measurement electrode 305 into the middle ear for positioning adjacent to the cochlea of a patient. In another approach, the electrocochleography measurement electrode 305 may be positioned within the middle ear of a patient via the same access surgically defined for implantation of the implantable transducer, e.g. transducer 108 in middle ear procedures.

Referring again to FIG. 3, the test device 302 may comprise a signal generator 306, a reference transmitter 308, a signal processing unit 310, a test control processor 312 and a user interface 314. By way of example, the test control processor 312 may provide signals for setting signal generator 306 to output reference signals at a predetermined frequency, or plurality of frequencies across a predetermined range, or an inherently broadband reference signal, e.g. a click. The output reference signals may be provided to the reference transmitter 308, which in turn outputs test signals to a given hearing instrument and the signal processing unit 310. The signal processing unit 310 stores the characteristics of the reference signals to assess the performance and positioning of the hearing instrument. In certain applications, it may be beneficial for the test control processor 312 to provide signals to the signal generator 306 to output reference signals that are swept across or inherently broadband to encompass a predetermined frequency range (e.g. a frequency range that encompasses a predetermined or determinable resonant frequency of an implantable middle ear transducer 108).

When used in conjunction with a semi-implantable hearing instrument system, the test signals from the reference transmitter 308 may be provided to the external wireless audio signal link transmitter/receiver 204 (e.g. via an input port as may normally receive a jack at the end of wire 202 for audio drive signal input from the microphone 208 and SSP processor 318). In turn, the external transmitter/receiver 204 transmits the test signals to the implanted receiver/transmitter 118, which provides the test signals to the implanted signal processor 104. The implanted signal processor 104 processes and supplies the test signals to drive the implantable transducer, e.g. transducer 108 in middle ear procedures.

When used in conjunction with a fully-implantable hearing instrument system, the test signals from the reference transmitter 308 may be provided to a speaker 320 for outputting acoustic test signals. In turn, an implanted microphone 322 may subcutaneously receive the acoustic test signals and provide output test signals to the implanted signal processor 104. In turn, the implanted signal processor 104 processes and supplies the test signals to drive the implantable transducer, e.g. transducer 108 in middle ear procedures.

As noted above, the electrocochleography measurement device 304 may provide measured electrical potential values to test device 302. More particularly, the measured potential values may be provided to the signal processing unit 310. In turn, the signal processing unit 310 may process the measured potential values in accordance with preset algorithms. For example, utilizing the stored reference signal information and stored algorithms corresponding with one or more of the above noted predeterminable ranges, the signal processing unit 310 may selectively extract the summating potential and/or action potential from the measured potential values. In turn, the extracted values may be averaged and/or otherwise successively compared to determine whether and when a predetermined threshold or maximum value is reached (e.g. thereby indicating a desired interface). Concomitantly, the values obtained via processing at signal processing unit 310 may be output (e.g. graphically displayed) at a user interface 314 so that medical personnel may utilize such output in conjunction with real-time positioning of the implantable transducer, e.g. transducer 108 in middle ear procedures. For example, during an implantation procedure, medical personnel may view user interface 314 to assess whether and when an implantable middle ear transducer 108 has been located to achieve the desired interface within the middle ear of a patient. In another approach, values obtained via processing at signal processing unit 310 may be utilized in conjunction with preset algorithms to provide a control signal to a transducer positioning means (e.g. a motor or piezoelectric positioner) to realize at least partially automated positioning of the implantable transducer. Further, following implantation the noted interface may be assessed from time-to-time by comparing currently measured values with previously measured values (e.g. the previously measured values having been obtained at the time of implantation).

Figure 5:
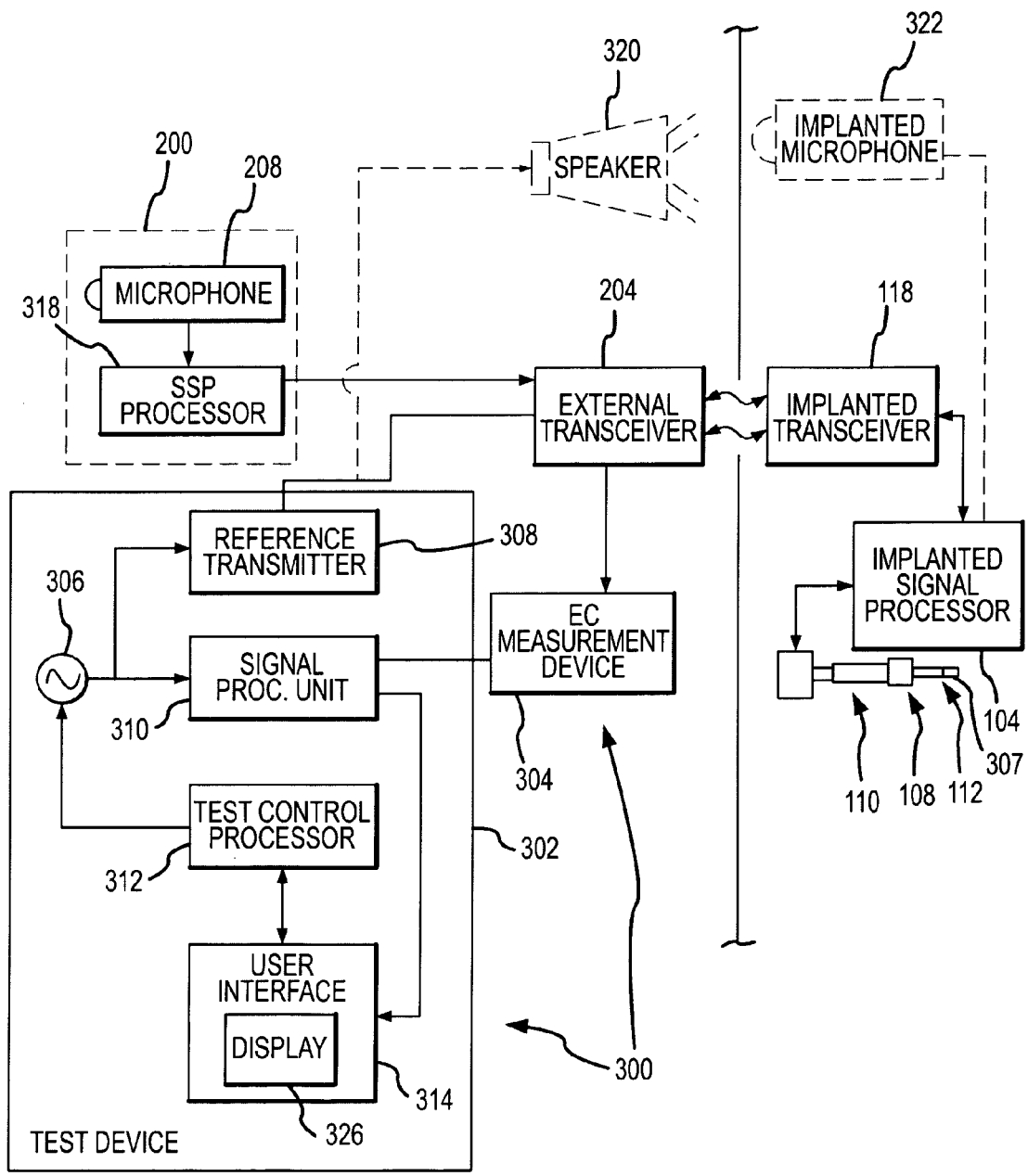
FIG. 5 illustrates another embodiment of the present invention that utilizes an electrocochleography measurement electrode that is disposed on the implanted transducer.

FIG. 5 schematically illustrates another electrocochleography measurement approach for measuring the summating potential and/or action potential. In this embodiment, an electrocochleography measurement electrode 307 may be disposed on the actuator 112 of an implantable transducer, middle ear transducer 108 as shown. In this regard, electrode measurement signals may be transmitted between the implanted signal processor 104 and electrode 307, wherein the potential values are transmitted by the implanted transceiver 118 to external transceiver 204. The potential values may then be provided to the electrocochleography measurement device 304 and the measured values may be outputted to test device 302. As may be appreciated, the electrocochleography measurement device 304 may be integrated into test device 302. Except for the operations noted above, the embodiment shown in FIG. 5 may otherwise be analogous to that described in relation to the embodiment of FIG. 3.

In a modified approach to that shown in FIG. 5, some or all of the functionality provided by electrocochleography (EC) measurement device 304 and/or test device 302 may be provided via implanted componentry. For example, implanted componentry may be interconnected with an implanted signal processor 104 to provide a test signal to an implantable transducer, e.g. middle ear transducer 108. Such test signal generation may be initiated on an automatic, periodic basis and/or pursuant to a user prompt signal provided via an external transmitter/receiver 204 to an implanted receiver/transceiver 118 in a semi-implantable hearing instrument system and provided via an external speaker 320 to an implanted microphone 322 in a fully-implantable system. Further, implanted signal processor 104 may be provided with processing logic as per signal processing unit 310, wherein measured potential(s) from electrode 307 are processed by signal processor 104 to yield an output indicative of or otherwise useful in assessing and/or establishing an interface between an implantable transducer and a middle ear component or inner ear of a patient. By way of example, such output may be externally transmitted by implanted transceiver 118 to external transceiver 204. In turn, such output may be provided to a user device (e.g. analogous to user interface 314).

Figure 6:
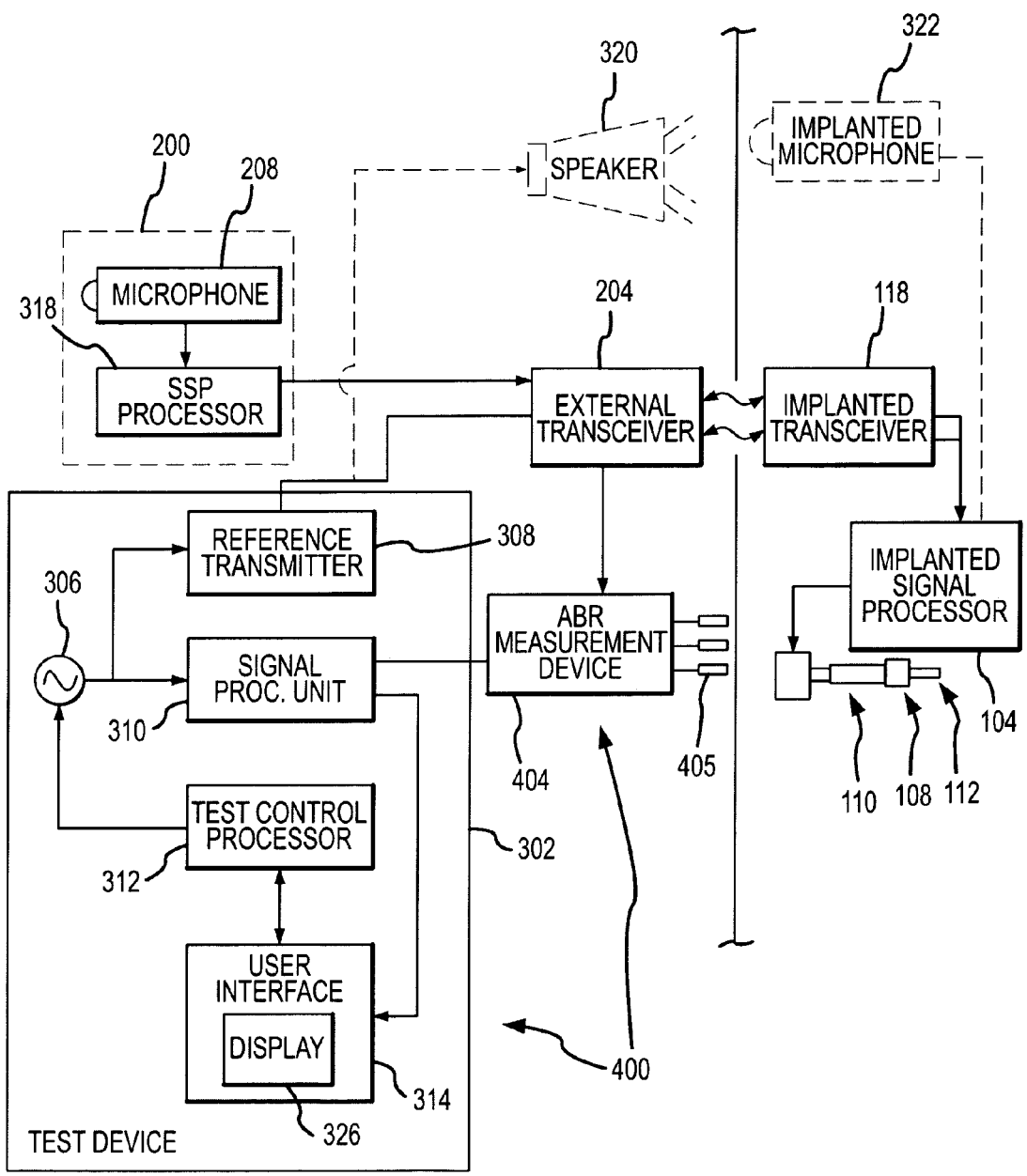
FIG. 6 illustrates another embodiment of the present invention that utilizes an auditory brainstem response measurement device to assess an interface between an implanted transducer and a middle ear component of a patient.
Figure 7:
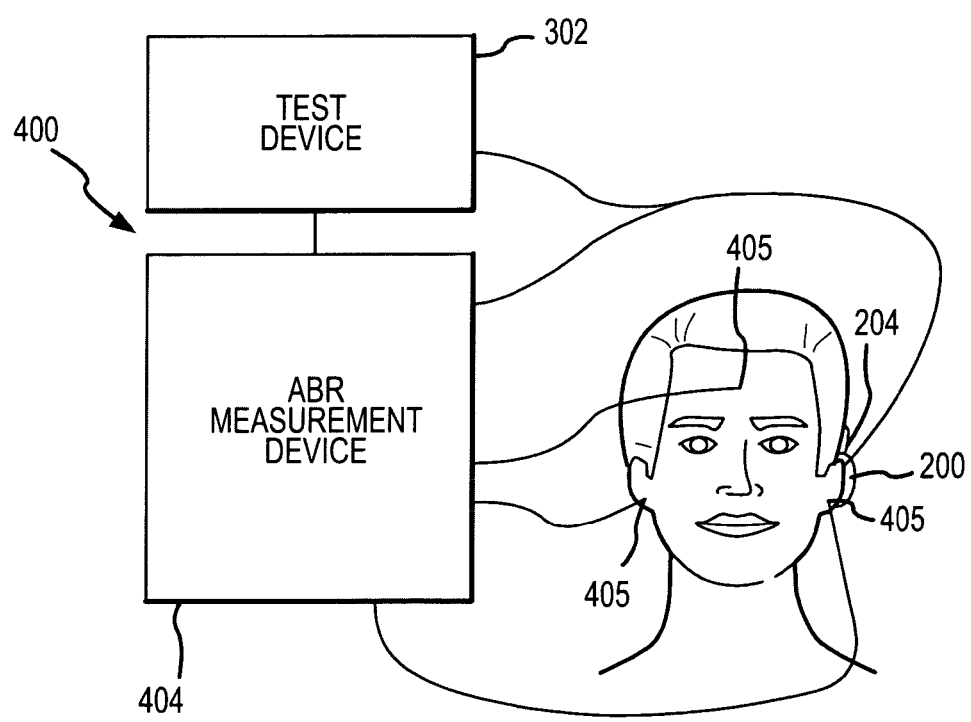
FIG. 7 illustrates auditory brainstem response measurement electrodes of the embodiment of FIG. 6.

Referring now to FIGS. 6 and 7, another embodiment of the present invention includes a measurement system 400 having a test device 302 and an auditory brainstem response (ABR) measurement device 404. The test device 203 is operable in a manner analogous to that described above. The ABR measurement device 404 measures the electrophysiological response in a predetermined area of the brain of a patient (e.g. the dorsal and ventral cochlear nuclei of the brainstem) pursuant to test signals that are generated by the test device 302 and supplied to the implanted transducer, (e.g., a middle ear transducer) 108. By way of example, and referring to FIG. 7, the ABR measurement device 404 may comprise one or more electrodes 405 for obtaining electrical potentials at various locations on a patient's scalp. In the illustrated arrangement, the ABR measurement electrodes 405 are located at the vertex of a patient's forehead and on the earlobes of the patient.

As may be appreciated, the electrical potentials obtained by electrodes 405 may be provided to the measurement device 404, and the measured values may be output to the test device 302 for processing. In this regard, predeterminable latency, durational and magnitude ranges may be utilized in one or more algorithms stored within the test device 304. Such predeterminable values and algorithms may be utilized in conjunction with processing the output of measurement device 404, thereby allowing for assessment of the implantable transducer interface with a middle ear component or inner ear of a patient in a manner analogous to that previously described.

As noted, the various features described above may be utilized for positioning an implantable transducer relative to an inner ear of a patient. In this regard, the implantable transducer, or a plurality of transducers, may be disposed on or within a flexible biocompatible carrier (e.g. comprising a bio-stable advanced polymer such as suitable silicones) that is advanced into position within the inner ear through an artificial opening of the cochlea or round window. In another approach, one or a plurality of output-side electromechanical transducers may be positioned extracochlearly. For example, the transducers may be positioned relative to an opening(s) or hole(s) defined in the bony wall bordering the cochlear so that a coupling element(s) attached to the transducer(s) may be advanced to project through the opening(s) into the lymphatic inner ear space. In yet another arrangement, an electromagnetic transducer approach may be utilized, wherein a magnet is applied to the outside of the round window membrane. In turn, an excitation device (e.g. one or more electrically conductive coils) may be positioned relative to the magnet to electromagnetically stimulate the magnet and thereby directly stimulate the inner ear.

The embodiments described above are for exemplary purposes only and are not intended to limit the scope of the present invention. Various adaptations, modifications and extensions of the embodiment will be apparent to those skilled in the art and are intended to be within the scope of the invention as defined by the claims which follow.

What is claimed:

1. A system for positioning an implantable hearing instrument transducer relative to a patient's middle ear component or inner ear, comprising:
   a signal source for supplying test signals to an implantable hearing instrument transducer as positioned at each of a plurality of different positions within a patient's middle ear or inner ear;
   an electrocochleography measurement device, interconnectable with said signal source, for measuring an electrical potential, associated with at least one of a cochlea and an auditory nerve of the patient, in timed relation to each of said test signals and for providing measurement signals in corresponding relation thereto; and,
   a processor for processing said measurement signals to provide an output relating to the desirability of at least one of said plurality of positions of said implantable hearing aid transducer.

2. The system of claim 1, wherein said processor output is indicative of the desirability of each of said plurality of positions of said implantable hearing aid transducer.

3. The system of claim 1, wherein said processor is adapted to compare at least one of the following:
   different ones of said measurement signals to provide said processor output; and,
   each of said measurement signals to at least one predeterminable value to provide said processor output.

4. The system of claim 1, wherein said processor is adapted to average a different plurality of said measurement signals in corresponding relation to each of a corresponding plurality of different time intervals, and to compare at least one of the following:
   different ones of said averages to provide said processor output; and,
   each of said averages to at least one predeterminable value to provide said processor output.

5. The system of claim 1, wherein said electrocochleography measurement device comprises:
   at least one electrode for measuring at least one of a cochlear microphonic, summating potential and auditory nerve compound action potential of the patient.

6. The system of claim 1, wherein said electrocochleography measurement device comprises:
at least one electrode for measuring an auditory brain stem response, in the form of an electrical potential, of the patient.

7. The system of claim 1, further comprising:
a user interface for receiving said processor output and providing a user interface output in response thereto, said user interface output providing an indication of the desirability of said at least one of said plurality of positions of said implantable hearing aid transducer.

8. The system of claim 7, wherein said user interface comprises at least one of the following:
an audio output device for providing an audio indication of the desirability of said at least one of said plurality of positions of said implantable hearing aid transducer to a user; and,
a visual output device for providing a visual indication of the desirability of said at least one of said plurality of positions of said implantable hearing aid transducer to a user.

9. The system of claim 8, wherein said user interface output provides an indication of the relative desirability of each of said plurality of positions of said implantable hearing instrument transducer.

10. The system of claim 8, wherein said processor and said user interface are adapted so that said user interface output provides a single indication in corresponding relation with the most desirous of said plurality of positions of said implantable hearing instrument transducer.

11. The system of claim 1, wherein said electrocochleography measurement device and said signal source are interconnectable so that, for each of said test signals, said electrocochleography measurement device only measures said electrical potential within a predetermined time range after the supply of each of said test signals.

12. The system of claim 1, wherein each of said test signals comprises a plurality of signal portions corresponding with different signal frequencies.

13. The system of claim 12, wherein each of said test signals has a signal frequency spread across a predetermined frequency range, said predetermined frequency range comprising a predetermined resonant frequency for said implantable hearing instrument transducer.

14. The system of claim 1, further comprising:
an automated positioner, interconnectable to an implantable hearing instrument transducer, for automatically positioning said implantable hearing instrument transducer in response to said processor output.

15. A method for positioning an implantable hearing instrument transducer relative to a middle ear component or inner ear of a patient, comprising:
supplying test signals to an implantable hearing instrument transducer located within a middle ear of a patient;
measuring an electrical potential associated with at least one of a cochlea and an auditory nerve of the patient in timed relation to each of said test signals to provide corresponding measurement signals;
processing said measurement signals to provide an output relating to the position of said implantable hearing aid transducer relative to a middle ear component or inner ear of the patient; and,
positioning the implantable hearing instrument transducer utilizing said output.

16. The method of claim 15, further comprising:
completing said supplying, measuring and processing steps successively for a plurality of times with said implantable hearing instrument transducer positioned at a corresponding plurality of different positions relative to the middle ear component or inner ear of the patient.

17. The method of claim 15, wherein said processor output is indicative of the relative desirability of each of said plurality of positions of said implantable hearing aid transducer.

18. The method of claim 5, wherein said processing step comprises at least one of the following:
comparing different ones of said measurement signals to provide said processor output; and,
comparing each of said measurement signals to at least one predeterminable value to provide said processor output.

19. The method of claim 15, wherein said processing step comprises:
averaging a different plurality of said measurement signals in corresponding relation to each of a corresponding plurality of different time intervals; and,
comparing at least one of the following:
different ones of said averages to provide said processor output; and,
each of said averages to at least one predeterminable value to provide said processor.

20. The method of claim 15, wherein said measuring step comprises:
locating at least one electrode relative to a patient to measure at least one of a cochlear microphonic, summating potential and an auditory nerve compound action potential.

21. The method of claim 20, wherein said locator step comprises:
positioning said at least one electrode within the middle ear of the patient.

22. The method of claim 20, wherein said positioning step comprises:
positioning said at least one electrode external to the patients corresponding eardrum.

23. The method of claim 15, wherein said measuring step comprises:
locating at least one electrode relative to a patient to measure an auditory brain stem response in the form of electrical potential.

24. The method of claim 15, further comprising:
providing a user interface output in response to said processor output, said user interface output providing an indication of the desirability of each of said plurality of positions of said implantable hearing aid transducer.

25. The method of claim 24, wherein said providing step comprises:
supplying an audio output to a user; and,
providing a visual output to a user.

26. The method of claim 15, further comprising:
synchronizing said supplying and measuring steps so that, for each of said test signals, said measuring step is completed within a predetermined time range after said supplying step.

* * * * *